United States Patent
Greter

(10) Patent No.: US 6,676,631 B1
(45) Date of Patent: Jan. 13, 2004

(54) VACUUM AND RATE CONTROL FOR A BREASTPUMP

(75) Inventor: Andy Greter, Steinhausen (CH)

(73) Assignee: Medela Holding AG, Baar (CH)

( * ) Notice: Subject to any disclaimer, the term of this patent is extended or adjusted under 35 U.S.C. 154(b) by 0 days.

(21) Appl. No.: 09/475,426

(22) Filed: Dec. 30, 1999

Related U.S. Application Data

(60) Provisional application No. 60/170,070, filed on Dec. 10, 1999.

(51) Int. Cl.[7] ................................................ A61M 1/06
(52) U.S. Cl. ........................................ 604/74; 604/118
(58) Field of Search ........................... 604/74, 346, 73, 604/75, 30, 135, 118, 119, 120

(56) References Cited

U.S. PATENT DOCUMENTS

| | | |
|---|---|---|
| 823,316 A | 6/1906 | Andersen |
| 1,259,309 A | 3/1918 | Somers |
| 1,644,257 A | 10/1927 | Lasker |
| 2,222,811 A | 11/1940 | Dinesen |
| 2,542,505 A | 2/1951 | Gascoigne |
| 3,238,937 A | 3/1966 | Stein ........................... 128/40 |
| 3,382,867 A | 5/1968 | Reaves ......................... 128/38 |
| 3,782,385 A | 1/1974 | Loyd ........................... 128/281 |
| 4,111,204 A | 9/1978 | Hessel ......................... 128/276 |
| 4,323,067 A | 4/1982 | Adams |
| 4,583,970 A | 4/1986 | Kirchner ...................... 604/74 |
| 4,607,596 A | 8/1986 | Whittlestone et al. |
| 4,673,388 A | 6/1987 | Schlensog et al. |
| 4,740,202 A | 4/1988 | Stacey et al. |
| 4,759,747 A | 7/1988 | Aida et al. |
| 4,794,915 A | 1/1989 | Larsson ....................... 128/64 |
| 4,857,051 A | 8/1989 | Larsson |
| 4,883,464 A | 11/1989 | Morifuki ..................... 604/74 |
| 4,886,494 A | 12/1989 | Morifuji |
| 4,929,229 A | 5/1990 | Larsson ....................... 604/74 |
| 4,961,726 A | 10/1990 | Richter |
| 4,964,851 A | 10/1990 | Larsson ....................... 604/74 |
| 5,007,899 A | 4/1991 | Larsson ....................... 604/74 |
| 5,049,126 A | 9/1991 | Larsson |
| 5,071,403 A | * 12/1991 | Larsson ....................... 604/74 |
| 5,100,406 A | 3/1992 | Panchula |
| 5,218,924 A | 6/1993 | Thompson et al. |
| 5,295,957 A | 3/1994 | Aida et al. |
| 5,571,084 A | * 11/1996 | Palmer ........................ 604/74 |
| 5,776,098 A | * 7/1998 | Silver et al. .................. 604/74 |
| 5,902,267 A | * 5/1999 | Medo .......................... 604/74 |
| 5,954,690 A | * 9/1999 | Larsson ....................... 604/74 |
| 6,139,521 A | * 10/2000 | Larsson ....................... 604/74 |

FOREIGN PATENT DOCUMENTS

| | | |
|---|---|---|
| AU | 121942 | 8/1946 |
| GB | 2 127 293 A | 4/1984 |
| WO | WO 99/44650 | 9/1999 |

* cited by examiner

Primary Examiner—Brian L. Casler
Assistant Examiner—Kevin C Sirmons
(74) Attorney, Agent, or Firm—Baniak Pine & Gannon

(57) ABSTRACT

A controller for a breastpump, such as a rotary knob, which is used to simultaneously adjust the suction level as well as rate within a sequence, is disclosed. The suction "force" and "speed" are tied together in an inverse relationship. As the suction force (vacuum) is increased, for example, the rate (cycle) is decreased; as the vacuum is decreased, the cycle increases.

3 Claims, 15 Drawing Sheets

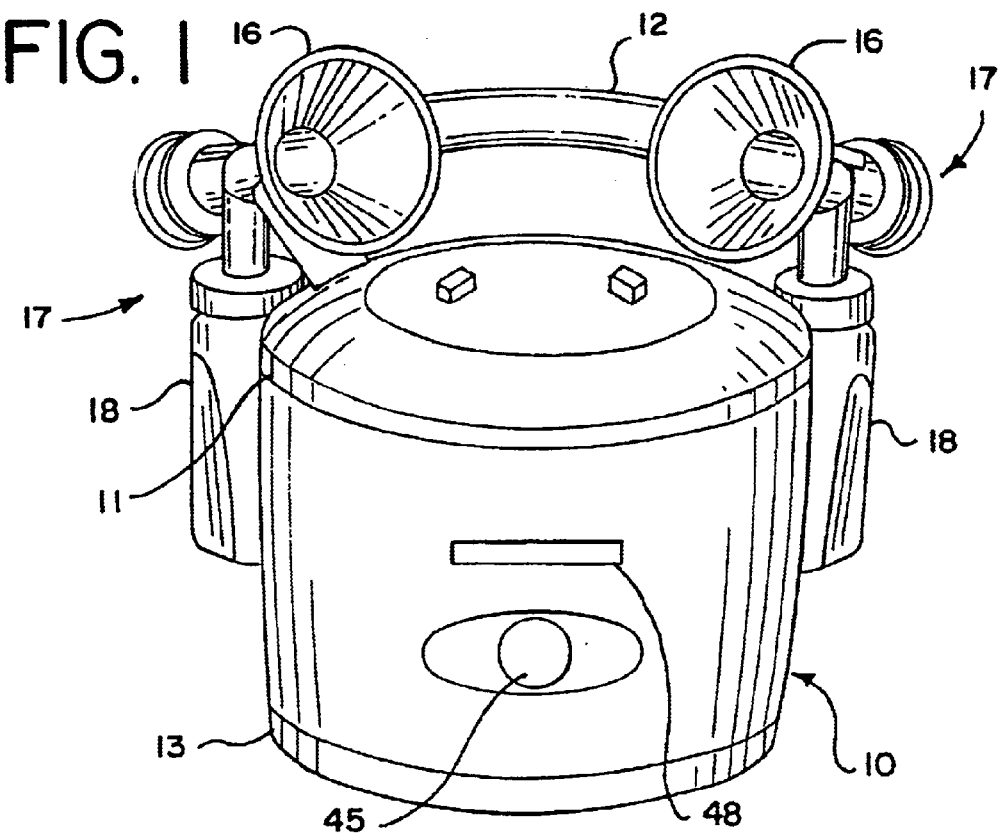
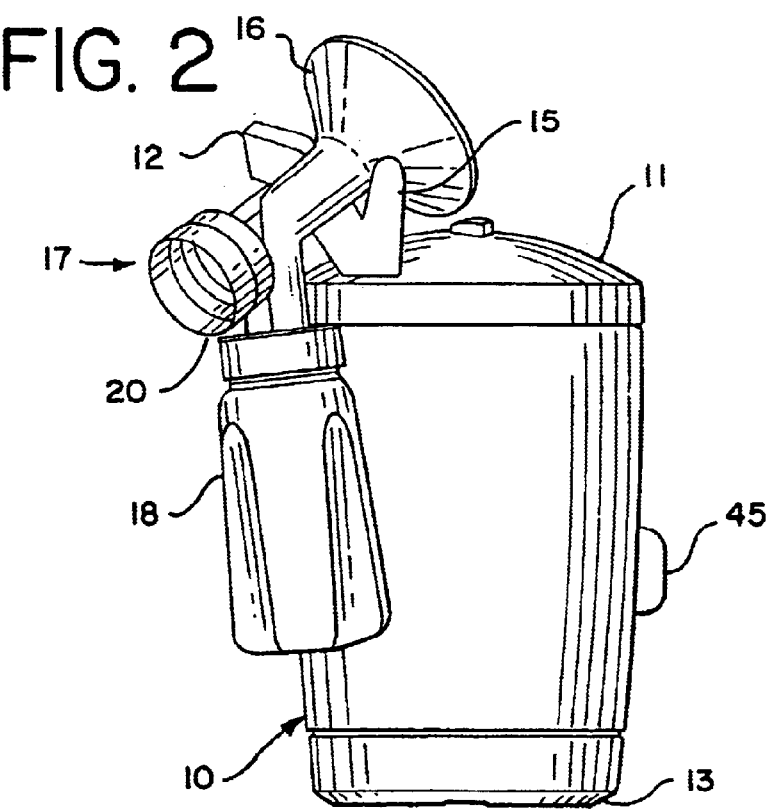

STANDARD CLASSIC PROGRAM

SUCTION CURVES AND CYCLES EQUAL TO CLASSIC
VACUUM RANGE: 100-250 mmHg
CYCLES: 47/min (NOT ADJUSTABLE)

SORE NIPPLE PROGRAM

EXTREMELY GENTLE AND SLOW SUCTION
DECREASED VACUUM YIELDS GENTLER AND SLOWER SUCTION
VACUUM RANGE: 20-250
CYCLES: 25-40/min (CONTROLLED BY VACUUM LEVEL)

FIG. 13

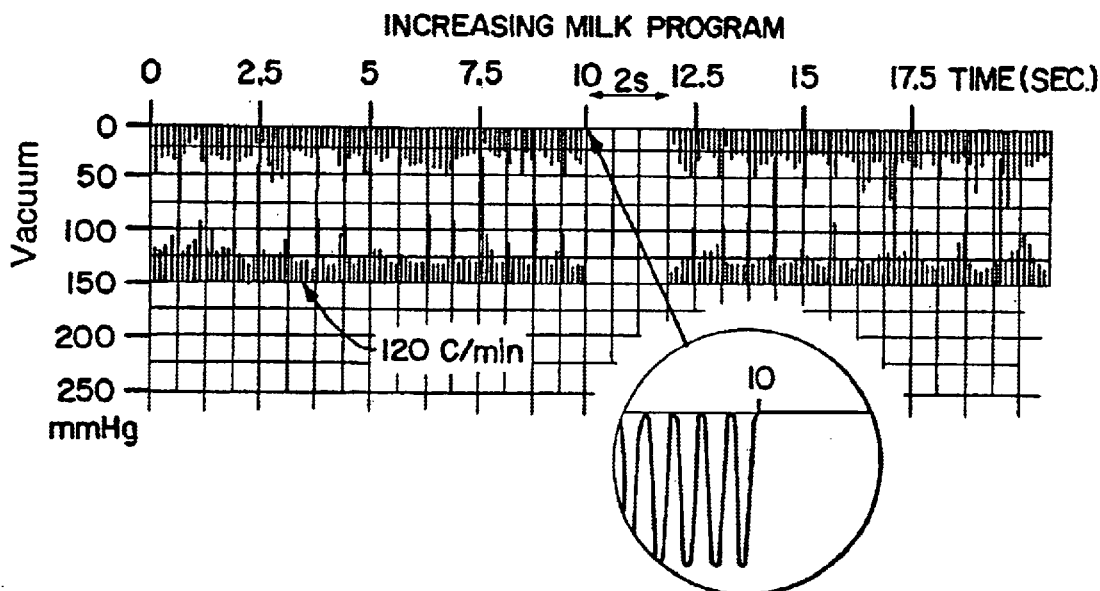

STIMULATION PROGRAM FOR INCREASING THE MILK PRODUCTION
IT IS USED BETWEEN THE PUMP SESSIONS A FEW TIMES A DAY
VACUUM RANGE: 50-150 mmHg
CYCLES: 120/min

FIG. 14

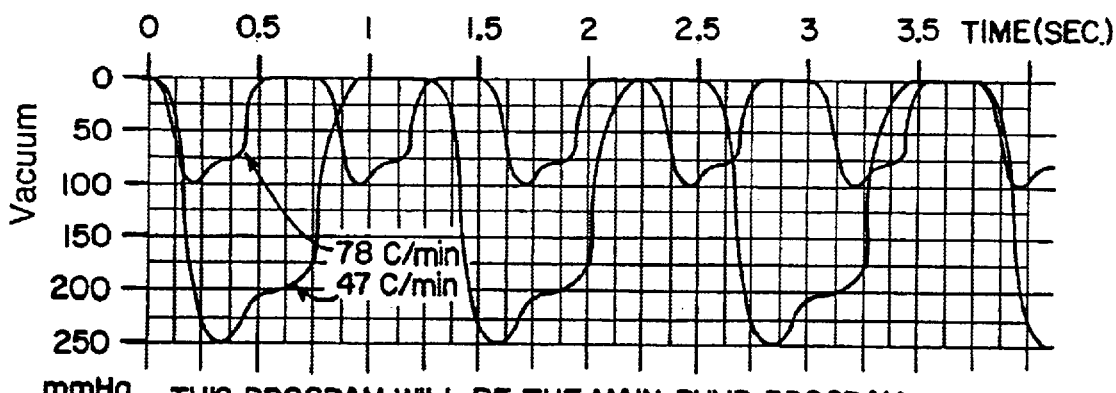

THIS PROGRAM WILL BE THE MAIN PUMP PROGRAM.
THE FINAL CURVE AND CYCLES HAVE TO BE
EVALUATED BY RESEARCHING.
VACUUM RANGE: 100-250 mmHg
CYCLES: 47-78/min AUTOMATICALLY THIS PROGRAM CONTAINS ALSO THE MILK LET DOWN PROGRAM
VACUUM RANGE: 50-150 mmHg
CYCLES: 120-150/min FIG. 17
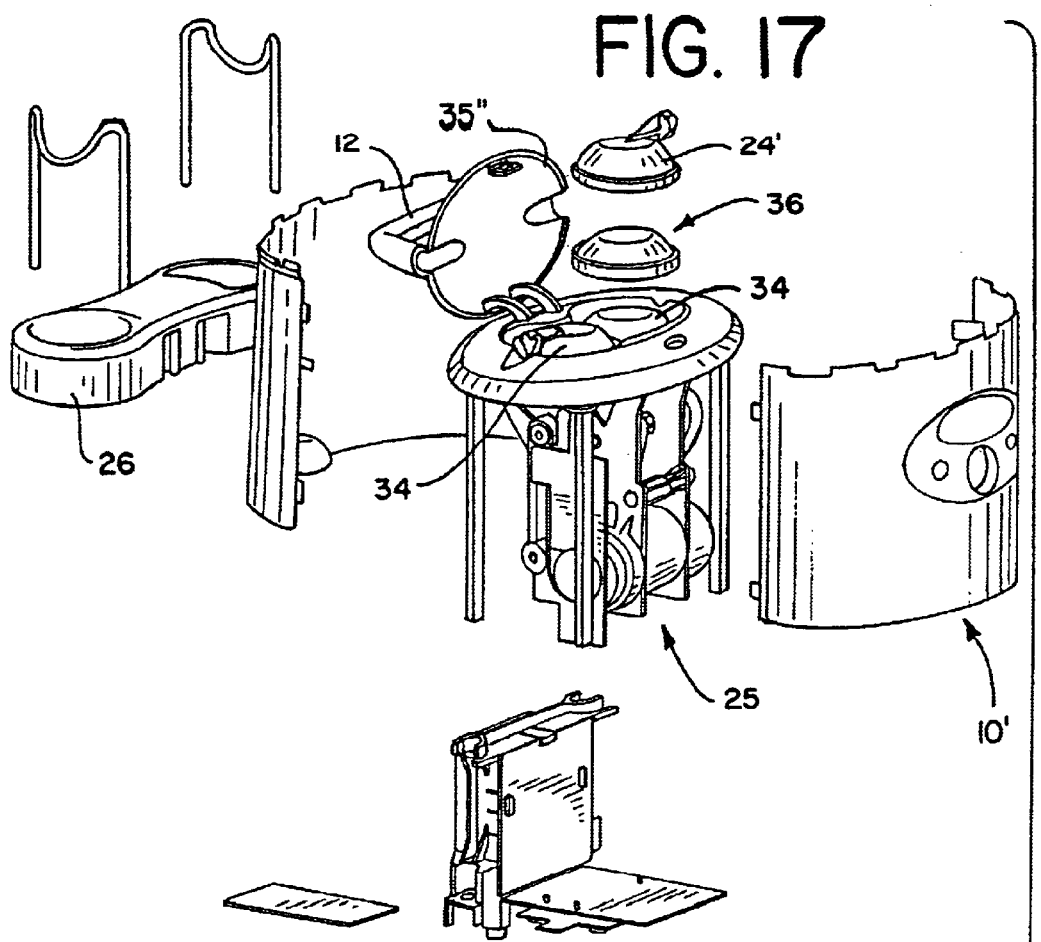
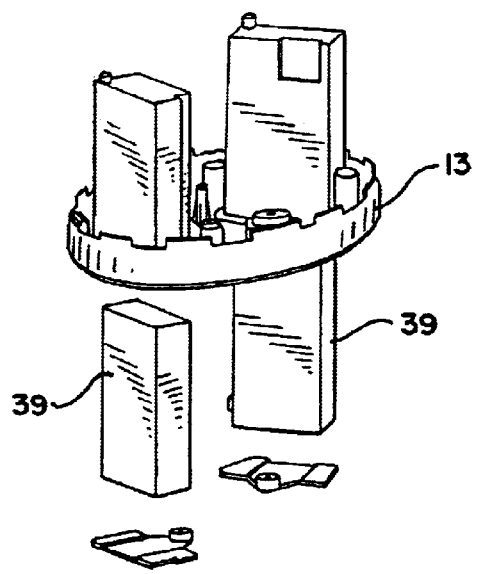

VACUUM AND RATE CONTROL FOR A BREASTPUMP

This application claims the benefit of Provisional application No. 60/170,070 filed Dec. 10, 1999.

FIELD OF THE INVENTION

This invention relates to breastpumps for drawing breastmilk, and particularly to a motorized, such as electrically driven, breastpump.

BACKGROUND OF THE INVENTION

Breastpumps for use by nursing mothers are well known. They allow the nursing woman to express the breastmilk as necessary or convenient, and further provide collection of the breastmilk for later use. For some mothers, breastpumps may be a necessity, such as when the child has suckling problems, or if the mother has problems with excessive or deficient milk production, or soreness, deformation or injury of the mammilla.

Manual breastpumps are commonplace, primarily because they are relatively inexpensive and easy to transport. Being manually driven, however, stroke rate and suction pressure produced can be uneven, and operating the pump can ultimately be tiring.

Electrically-driven breastpumps are also commonplace. They may be of a substantially large size of a non-portable or semi-portable type, typically including a vacuum pump which has an electric motor that plugs into standard house current. Advantages of this type of pump are ready controllability and regulation of the vacuum, and the ability to pump both breasts at once. That is, the nursing woman has both hands free to hold two breastpump shields in place for pumping of both breasts at the same time.

Battery-driven breastpumps have also been developed. These breastpumps have the advantages of controllability and regulation of the vacuum, as well as being easily carried. Such a battery-driven portable breastpump is described in U.S. Pat. No. 4,964,851, for example. This breastpump, sold under the name MINIELECTRIC by Medela, Inc., is lightweight and achieves good vacuum (i.e., negative pressure) regulation in preferred limits, for example, between about 100 and about 220 mmHg. The LACTINA breastpump sold by Medela, Inc. is also another type of breast pump which may be driven by battery as well as house current. It is generally disclosed in U.S. Pat. No. 5,007,899.

Electrically driven motorized breastpumps have almost universally been developed with a single type of "cycle" for a given pump. That is, the driving mechanism for generating the vacuum (negative pressure) to be applied at the breast in the more sophisticated pumps is geared to a particular sequence, or curve, of negative pressure increase (i.e., increasing suction), and then release. This is often aimed at reproducing in some sense the suckling action of an infant, for instance. Breastpumping can cover a range of different conditions, however, such as where the mother's nipples are sore for some reason, there is a state of significant engorgement, some nipple stimulation may be particularly desired, let-down and relaxation may be of particular interest, it may be desired to increase milk production, and so on.

Some breastpumps provide the user with the ability to vary the amount of vacuum being applied, as well as the speed of the pumping action (i.e., number of cycles per minute). In some instances in the prior art, speed and vacuum level may influence each other, such that as speed increases so does the vacuum level. The basic "curve" remains fixed, however, and the user must adapt as best she can to making variations within that particular curve built into the machine, which typically has been generalized for the overall population of users.

SUMMARY OF THE INVENTION

It is a principal objective of the present invention to provide a breastpump which can be programmed to generate, among other things, a plurality of differing milk expression (extraction) sequences, or curves. To this end, the invention in one form is a breastpump comprising a breastshield having a portion within which a woman's breast is received for the expression of milk. A source of vacuum is in communication with the breastshield. There is a mechanism for operating the source of vacuum according to a first sequence, and a controller for operating the source of vacuum according to a second sequence.

The controller can have a preset program for the second sequence which is a milk letdown sequence, for example. Preferably, the breastpump has a plurality of different programs for the controller wherein each program has a different sequence.

In one embodiment of the invention, a motorized pump (e.g., compressed air, battery and/or house current) is provided with a microprocessor-based controller. Cards, with memory "chips," containing different suction curves adapted for varying conditions and objectives are included for programming the controller in this embodiment. A user selects a desired program, and that card is then read by a mechanism providing input to the controller. It should be noted that while suction curves are generally addressed in the first instance herein, the milk expression sequences may also include a positive pressure aspect. The programming could also be provided via other media, including discs, CDs, infrared data transfer, electronic feed (e.g., an Internet connection), and so forth.

A significant, and heretofore unavailable advantage realized by the present invention is the ready ability to modify the breastpump suction action to a variety of desired conditions, and provide this ability to the end-user. An attendant advantage is that, as the science of breastpumping continues to make advances, new and improved suction curves and sequences can be made available on further cards, or other program-inputting means.

Yet another attendant advantage is that the programmable pump can also record data relating to its use and operation. That data could be stored, for instance, and then retrieved as by downloading through an Internet connection, magnetic recording (disk or card), and the like. This data retrieval would be useful in medical research, for updating the pump with new data, for monitoring usage, just for some instances.

Further, a program could be made of a particular infant's suckling pattern. That program could then be used to operate the pump, and then varied over time as the infant grows.

In yet another aspect of the invention, an improved breastpump is provided which has a pre-programmed milk let-down sequence. The let-down sequence is most advantageously made available through a button or the like provided on the breastpump used to actuate the sequence.

In still another aspect of the invention, a breastpump includes an electric motor having a reduction gear system with at least first and second belts conveying motive power to a movable member of an expansible chamber device wherein a vacuum is generated. The expansible chamber device is, in one embodiment, a pair of diaphragm pumps. Each diaphragm pump has a membrane which is movable relative to a shell, each said membrane being connected to a respective drive shaft, each shaft being mounted to a respective belt for linear movement with the respective belt.

The present invention in another significant aspect has as an objective to provide a breastpump with one or more novel suction sequences which are considered to produce advantageous particularized results. Such sequences include, but are not limited to: a suction method (e.g., program or curve) for a sore nipple condition; a suction method for increased milk production; an improved suction method in general; and a method for nipple stimulation.

A method for operating a breastpump for a sore nipple condition according to the present invention comprises varying the amount of vacuum within a range of from about 20 mmHg (the least vacuum) to about 250 mmHg (the greatest vacuum) while simultaneously varying the overall suction cycle from about 25 cycles/min. at the least vacuum to about 40 cycles/min. at the greatest vacuum, such that for a lower vacuum applied there is an increase in the number of cycles. In general, this program is intended to provide a lower peak vacuum over a longer cycle.

A method for operating a breastpump which is considered to yield an increase in milk output according to the present invention comprises operating the pump at a rapid cyclical rate on the order of about 120 cycles/min., with a negative pressure in the range of about 50 to about 150 mmHg. This method further preferably includes a pause after each period of vacuum application, such as applying the vacuum for about ten seconds of vacuum, with then a two second pause.

A method for operating a breastpump according to yet another aspect of the invention comprises varying the vacuum within a range of about 100 (the least vacuum) to about 250 mmHg (the greatest vacuum), while simultaneously varying the overall suction cycle from about 47 cycles/min. at the greatest vacuum to about 78 cycles/min. at the least vacuum, such that for a lower vacuum applied there is an increase in the number of cycles, with a cycle following a curve which initially builds to a peak negative pressure, then smoothly starts a pressure increase (less negative) along an initial slope but then slows the pressure increase briefly, before continuing on essentially said initial slope for the negative pressure release.

A still further aspect of the present invention is a unique breastpump assembly having features including: a compact housing design and breastshield carrying casing; and a double-diaphragm pumping mechanism.

A prophylactic device for protecting the diaphragm from fluid (air/milk) is additionally provided. In one embodiment of this aspect of the invention, a diaphragm pump for a breastpump comprises a shell having a generally hemispherical interior shape with a flexible membrane movable within the hemispherical shape to expand and contract a volume created in a chamber defined between the membrane and the shell. A mechanism connected to the membrane, such as a puller, moves the membrane to expand and contract the volume. A port is provided in the shell through which air moves in response to expansion and contraction of the volume, such that vacuum can be communicated to a breastshield through connection to the port.

A removably mounted flexible cover is located between the shell and the membrane which isolates the membrane from fluid. The cover is removable for at least one of cleaning and disposal. To that end, the flexible membrane has a circumferential rim upon which the cover is received over the rim. The shell has an internal opening defined therein sized to encompass the rim with the cover mounted on the rim in a substantially airtight fit. The cover thereby forms a gasket between the rim and shell. A one-way valve extending through the membrane is additionally provided, allowing exhaustion of air between the membrane and cover.

Yet another significant aspect of the present invention is considered to be a manually operated control, such as a rotary knob, which is used to simultaneously adjust the suction level as well as rate within a sequence. In this aspect of the invention, the suction "force" and "speed" are tied together in an inverse relationship. As the suction force (vacuum) is increased, for example, the rate (cycle) is decreased; as the vacuum is decreased, the cycle increases.

These and other features and advantages of the present invention will be further understood and appreciated when considered in relation to the following detailed description of embodiments of the invention, taken in conjunction with the drawings, in which:

BRIEF DESCRIPTION OF THE DRAWINGS

FIG. 1 is a front perspective view of a breastpump assembly made in accordance with aspects of the present invention;

FIG. 2 is a side elevational view of the breastpump of FIG. 1;

FIGS. 11 through 14 are various methods (curves) for operating the breastpump to differing ends;

FIG. 17 is a somewhat exploded assembly view of the major components of yet another breastpump made in accordance with the present invention;

DETAILED DESCRIPTION OF EMBODIMENTS OF THE INVENTION

The Breastpump Assembly

Figure 3:
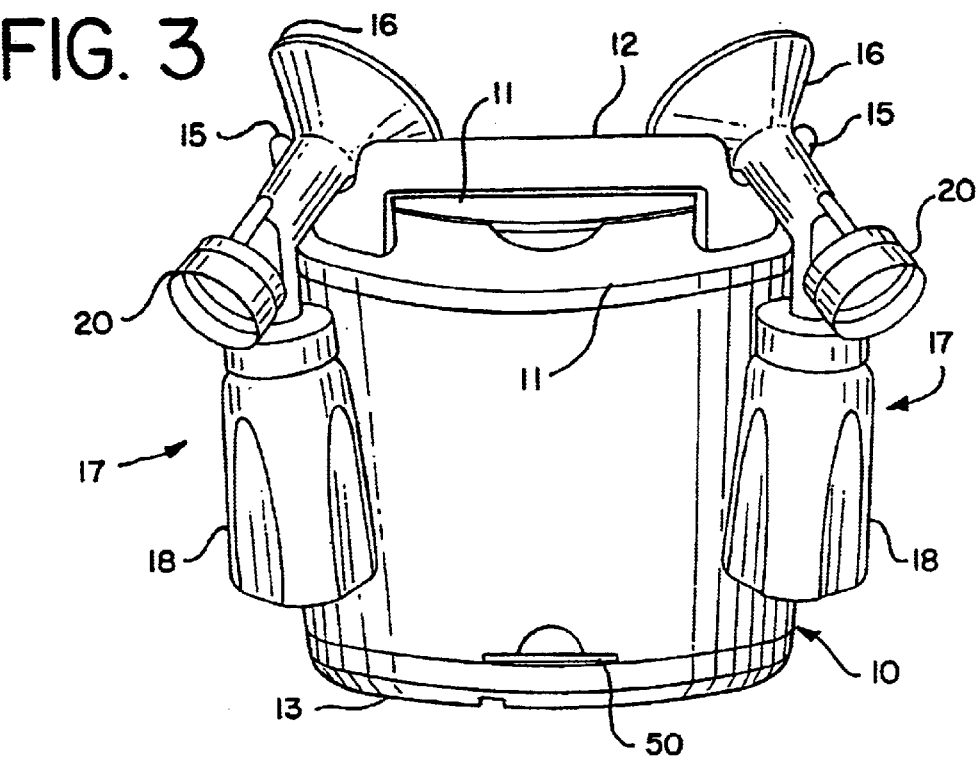
FIG. 3 is a rear perspective view of the breastpump of FIG. 1.
Figure 4:
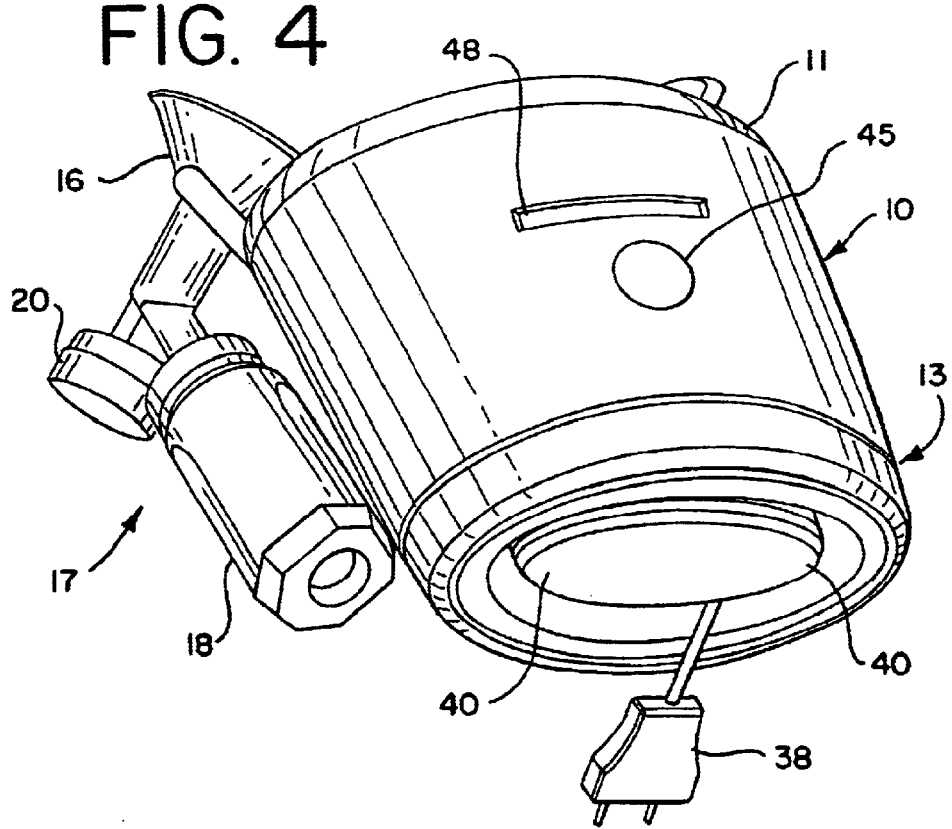
FIG. 4 is a perspective view of the breastpump of FIG. 1 looking at the bottom.
Figure 5:
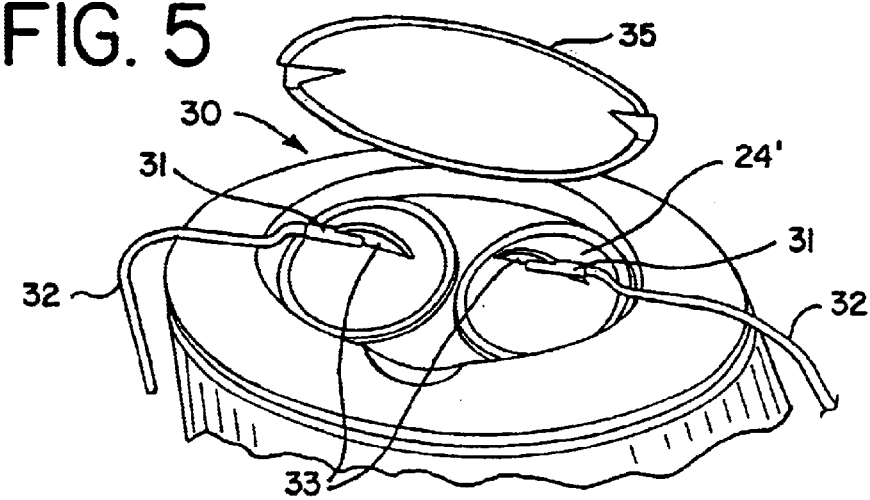
FIG. 5 is a top view of the breastpump of FIG. 1 with a cover removed revealing diaphragm pumps.
Figure 6:
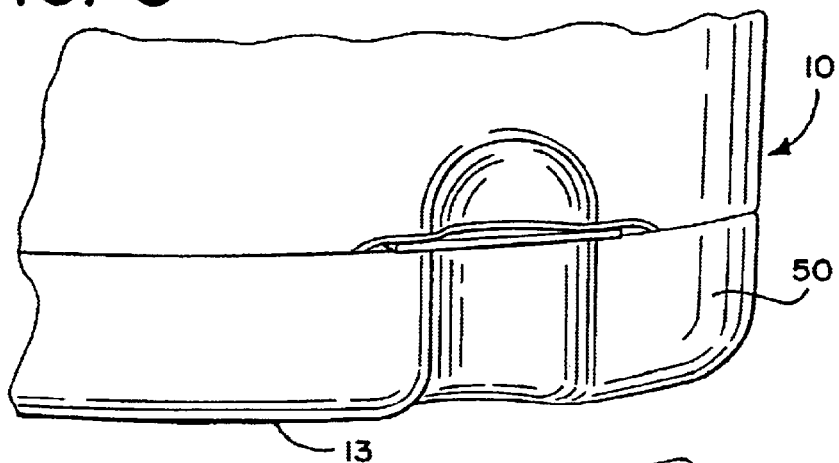
FIG. 6 is an enlarged side view of the breastpump of FIG. 1 adjacent the bottom highlighting the program card insert slot.

Referring to FIGS. 1 through 7 initially, a breastpump assembly of the present invention in one form has an aesthetically pleasing and compact design. The housing for the major components of the assembly is a casing 10 made of a rigid high impact plastic. As shown, it has a generally ellipsoidal cross-section along its vertical axis, yielding a pleasing smooth curving look to the casing exterior. The casing 10 is closed at its upper end by an upper housing part 11, to which is affixed a carrying handle 12.

In this first embodiment, carrying handle 12 has a pair of cradles 15 formed in opposite ends thereof. These cradles 15 are adapted to receive and support the funnel portions 16 of respective breastshields 17. These breastshields 17 (sometimes referred to themselves as breastpumps) are of the type shown and described in U.S. Pat. Nos. 4,964,851 and 4,929,229, for instance. Further detail regarding the breastshields 17 may be obtained through reference to those patents, but will be omitted herein since the inventive features in point in this application are not contingent upon the breastshield being used, so long as it is suitable to the task of milk expression.

In general, however, the breastshields 17 have the aforementioned funnel portion 16 which communicates with conduit structure connecting to a container (bottle) 18. This particular breastshield 17 is adapted for both manual as well as motorized pumping. It has a collar 20 to which a manually-driven piston pump (not shown) is screw-threaded for attachment and use in one mode of operation. When an electrically operated vacuum pump is to be employed, there is a port provided inside of the collar 20 which is in communication with the funnel portion, and to which a tube from the vacuum pump is releasably connected to convey vacuum to the breastshield. Again, such detail is well known, and can be gleaned from the foregoing patents, among other public sources. In operation in either mode, the widened (conical) portion of the breastshield 17 is placed on the breast for drawing vacuum within the shield, and thereby drawing milk through a pulling force applied to the breast. Milk drawn from the breast is collected in the bottle 18.

Figure 15:
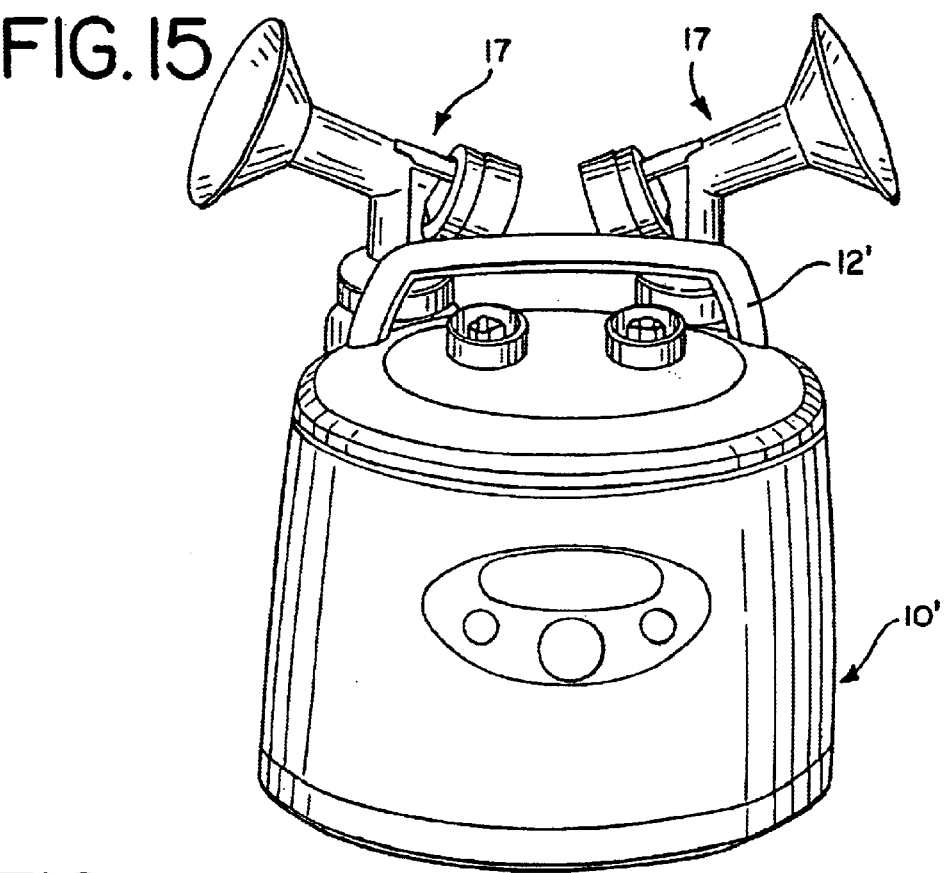
FIG. 15 is a front perspective view of another embodiment of a breastpump assembly made in accordance with aspects of the invention.
Figure 16:
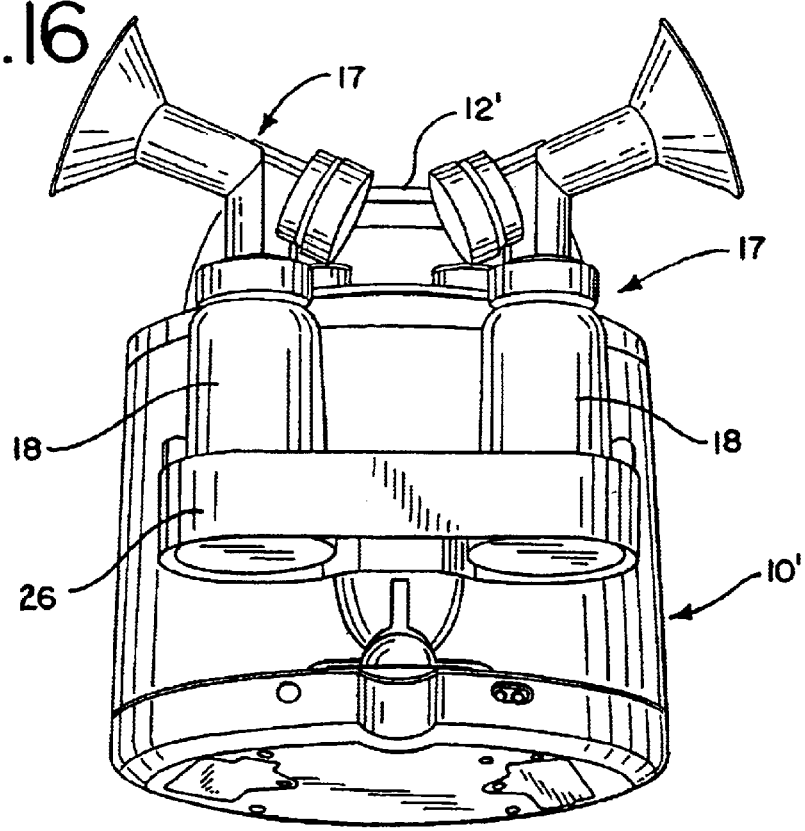
FIG. 16 is a rear perspective view of the FIG. 15 embodiment.
Figure 19:
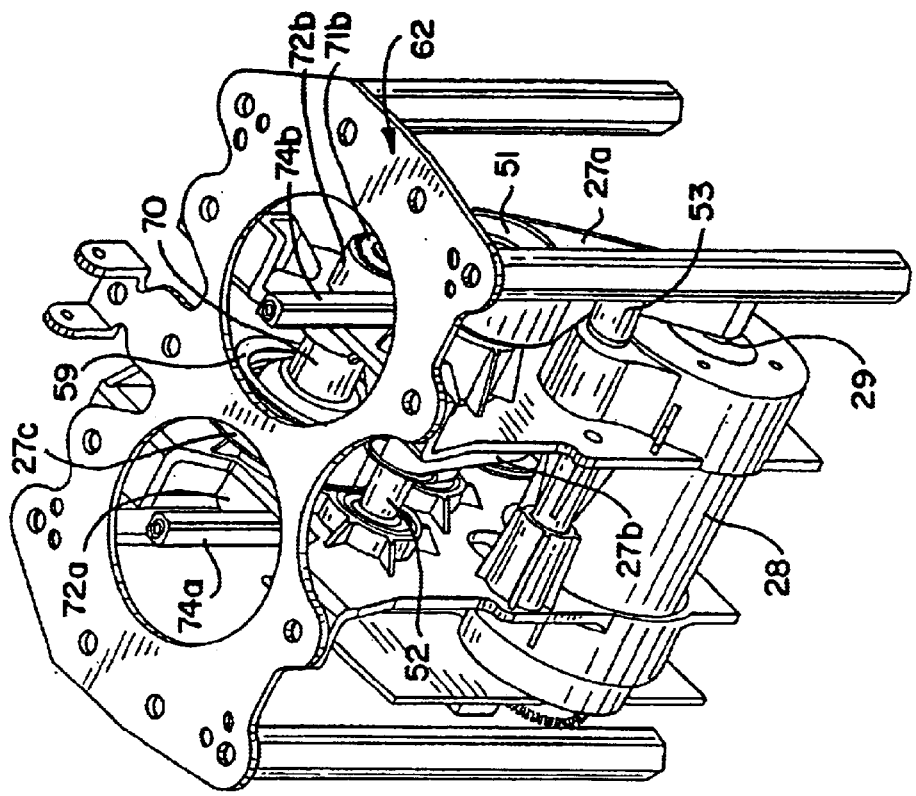
FIG. 19 is a view similar to that of FIG. 18 but from a top perspective.
Figure 18:
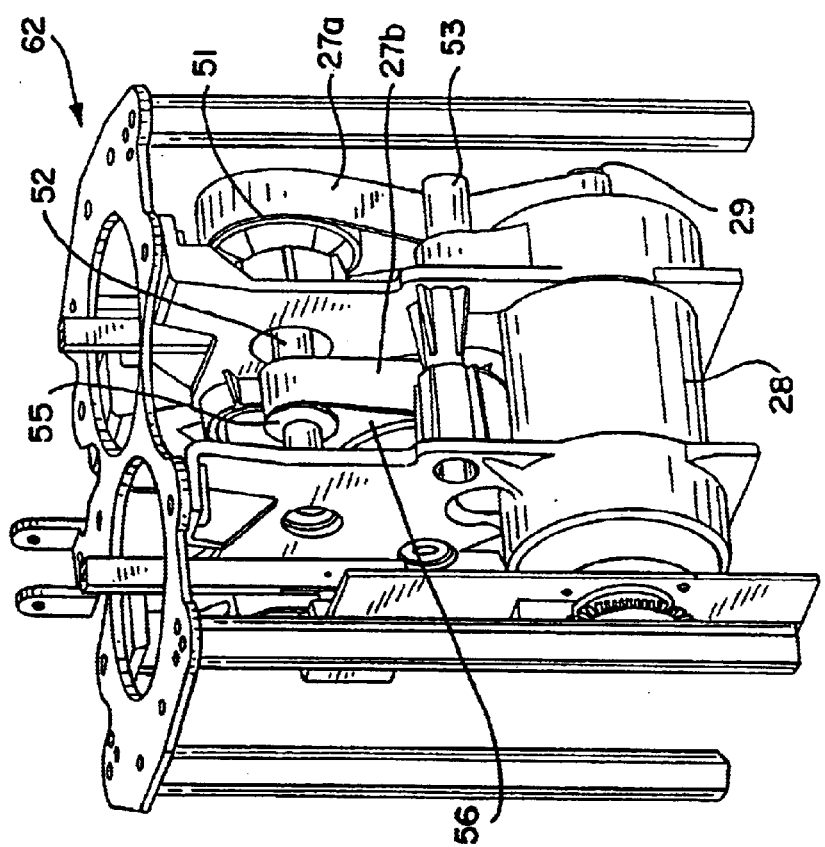
FIG. 18 is an enlarged front perspective view of the motor drive of the breastpump of FIG. 17.

FIGS. 15 and 16 show a modified exterior for the breastpump 10' (prime numbers being used herein to refer to similar but modified parts). In this version the breastshields 17 are not cradled by the handle 12', but instead are carried in a holder 26 mounted to the back of the unit.

The Drive Motor

Figure 8:
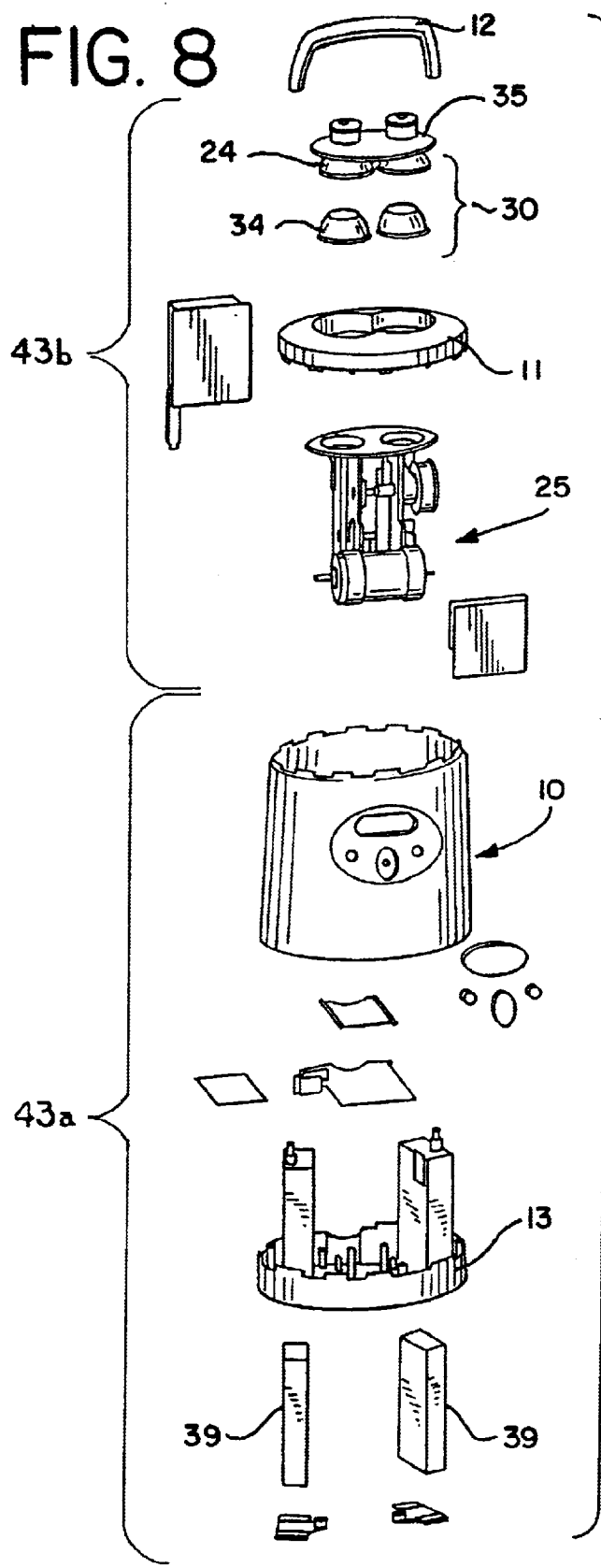
FIG. 8 is a somewhat exploded assembly view of the major components of the breastpump of FIGS. 1 through 5, with a modified top cover for the diaphragm pump assembly.

Referring to FIG. 8 initially, casing 10 has a drive unit 25 mounted therein. There are, of course, any number of drives that may be used for diaphragm pumps such as those used in the instant embodiment. Indeed, the type of pump (diaphragm, piston, etc.) is not necessarily significant to certain aspects of the present invention. The driving mechanism for the breastpump shown for the embodiment in point, however, is a linear drive for the diaphragm pumps consisting of a reduction drive arrangement and a 12 V DC-motor 28.

It will be noted that the FIG. 8 embodiment is substantially the same as that of FIGS. 1 through 7, except for a modified cover for the upper housing, which here includes the rigid shells 24 for the diaphragms 34 as part of the cover 35. The diaphragm pumps 30 will be further described hereafter.

FIG. 17 shows yet another version of a breastpump of the present invention substantially the same as that of FIGS. 1 through 8, except with a modified cover 35" and shell 24" for the diaphragm pump 30. The breastshield holder of the FIGS. 15 and 16 embodiment has also been slightly modified. It is with respect to this FIG. 17 embodiment that the majority of the interior detail of the breastpump will be further understood.

Turning now to FIGS. 18, 19 and 22 through 24 in particular, the reduction gearing contains belts 27a, 27b and 27c. Power is transferred from the shaft 29 of motor 28 to belt 27a. Belt 27a is received in a channel of wheel 51, which is mounted to the drive chassis 62 on rotatable shaft 52. Shaft 52 is fixed to rotate with wheel 51. A freewheel 53 is mounted on a shaft 54 fixed to the chassis 62 to freely rotate, and engages the outside of belt 27a, producing more surface engagement by the belt 27a with wheel 51.

Figure 22:
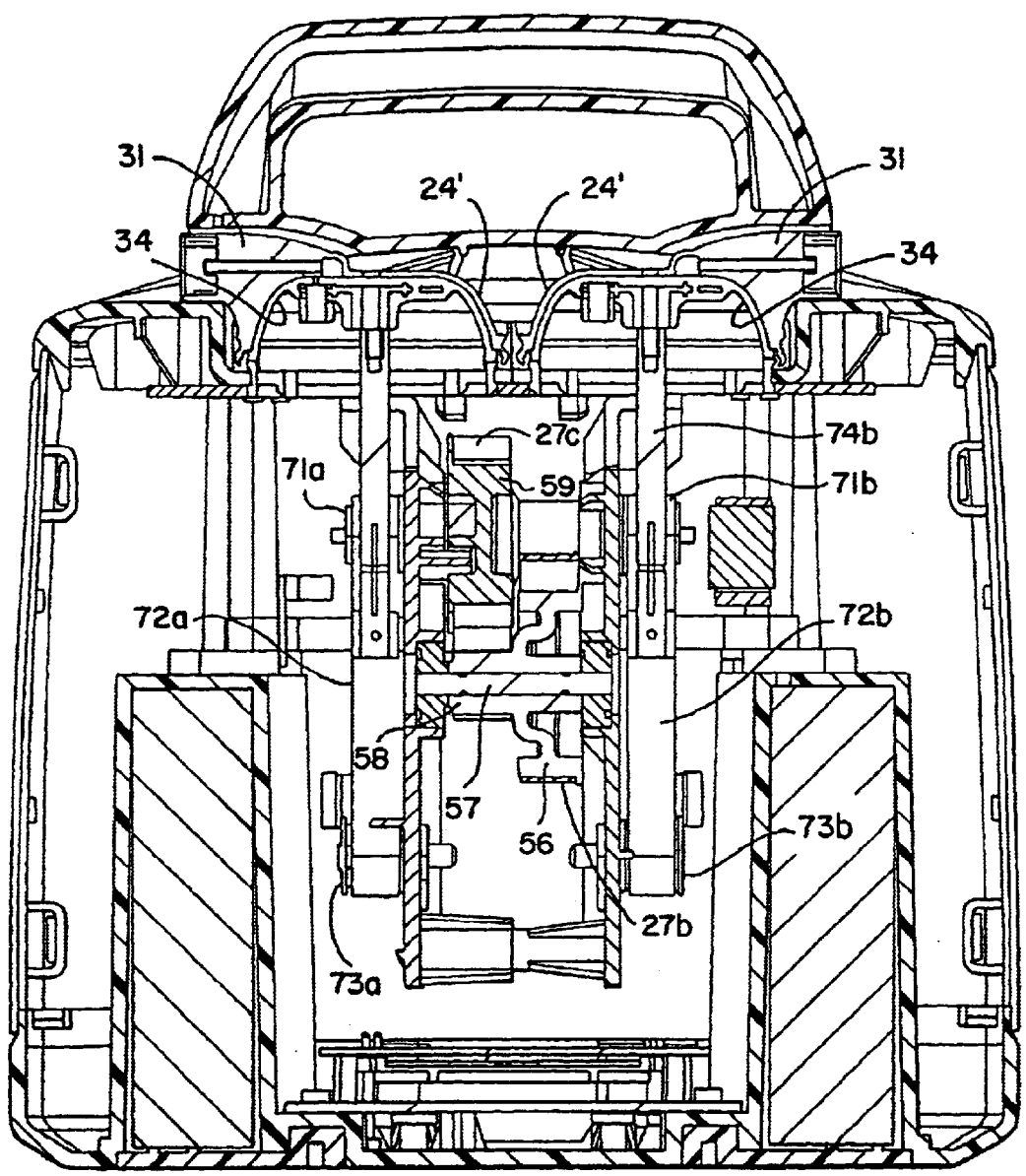
FIG. 22 is a sectional view of the assembled breastpump of FIG. 17 taken through the middle of the breastpump along its long lateral axis (side to side) looking rearwardly.
Figure 23:
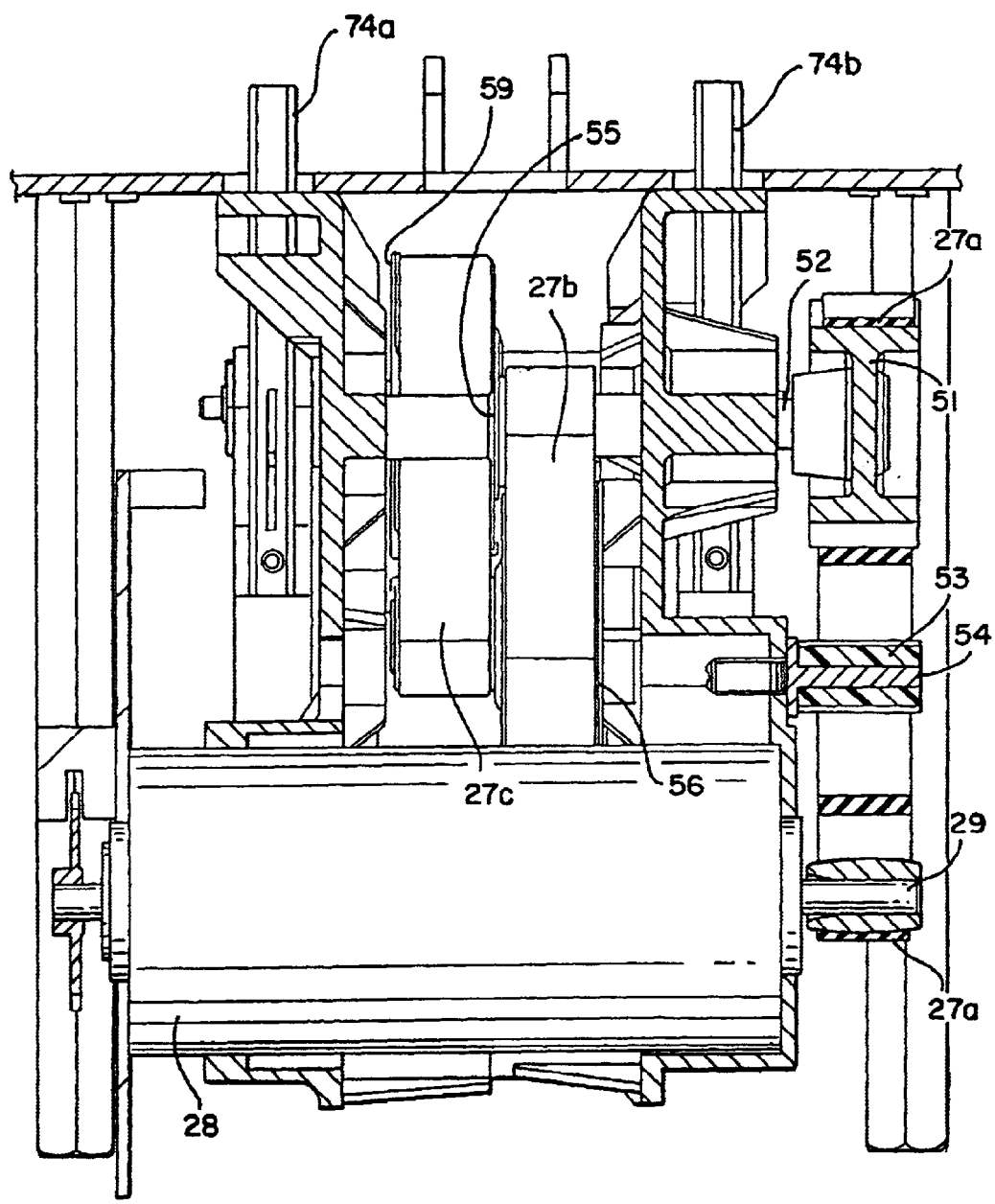
FIG. 23 is a sectional view similar to that of FIG. 22 taken along a plane forwardly of that of FIG. 22.
Figure 24:
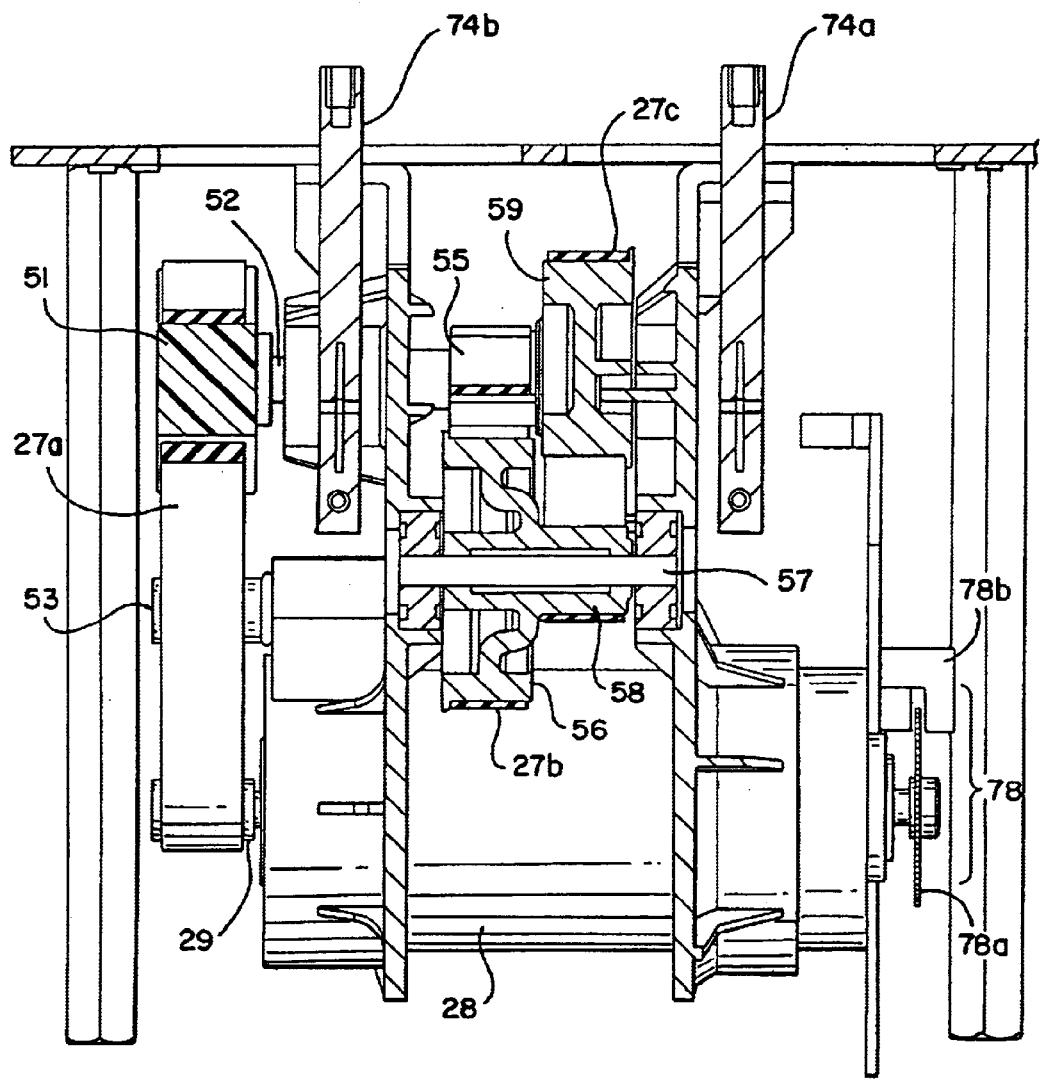
FIG. 24 is a sectional view similar to that of FIG. 22 taken along a plane behind the electric motor looking back to front.

Shaft 52 has a small toothed gear 55 mounted thereon. Belt 27b is toothed, and engages the gear 55. Toothed belt 27b furthermore engages a larger toothed gear 56 fixed to rotating shaft 57 (FIGS. 22 and 24). Part of gear 56 is small toothed gear portion 58. Belt 27c, which is also toothed, engages gear 58 as well as toothed gear 59. Gear 59 is fixedly mounted to rotating shaft 70. Fixed at each end of shaft 70 are small toothed gears 71a, 71b. Toothed belts 72a, 72b respectively engage gears 71a, 71b and freely rotating toothed gears 73a, 73b.

Diaphragm pusher (push/pull) shafts 74a, 74b are respectively clamped to belts 72a, 72b at one end. The other end engages the interior of a respective diaphragm membrane member 34 (FIG. 22, and also see FIGS. 20 and 21(a)). Here, a screw engagement with the shafts 74a, 74b was used, with a threaded nut-like element 37 mounted in a reinforced central area of membrane 36 (again, the diaphragm pumps 30 are described in more detail below). Both of the pusher shafts 74a, 74b move in tandem as driven by respective belts 72a, 72b.

Accordingly, as motor drive shaft 29 turns, belt 27a rotates shaft 52 via wheel 51. Belt 27b is in turn thereby driven off of smaller gear 55, causing rotation of shaft 57, which in turn rotates larger gear 56 and its smaller part 58, to thereby turn shaft 70 via belt 27c which couples gear part 58 with larger gear 59. This transfers the motion via gears 71a, 71b to belts 72a, 72b, imparting a linear movement to the pusher shafts 74a, 74b. A forward and then backward stroke is generated, through reversal of the motor shaft 29 direction. Reduction gearing is thus obtained as desired through appropriate selection of the various gears/wheels noted above.

The location of the shafts 74a, 74b along the path of travel, as well as the length of the stroke, is measured by position sensing mechanism 78, which can be of any standard and well known variety. This sensing mechanism 78 uses a toothed wheel 78a mounted to the shaft 29 of motor 28, which is registered by counter 78b. Signals generated by the counter 78b are processed by the cpu of the breastpump.

A negative pressure, or vacuum, is generated in a pair of diaphragm pumps 30. Each diaphragm pump has a flexible membrane 34 mounted in the upper housing 11 assembled with a respective rigid shell 24 (and see FIGS. 20 and 21(*a*) through 21(*c*) described further below). The membrane and shell are in substantially airtight engagement. When the membrane 34 is pulled away from the shell 24, a vacuum is generated in the space between the shell interior and the membrane, which can be accessed through outlet port 31 formed on the shell, to which a tube 32 is connected to communicate the vacuum to a respective breastshield 17.

Figure 7:
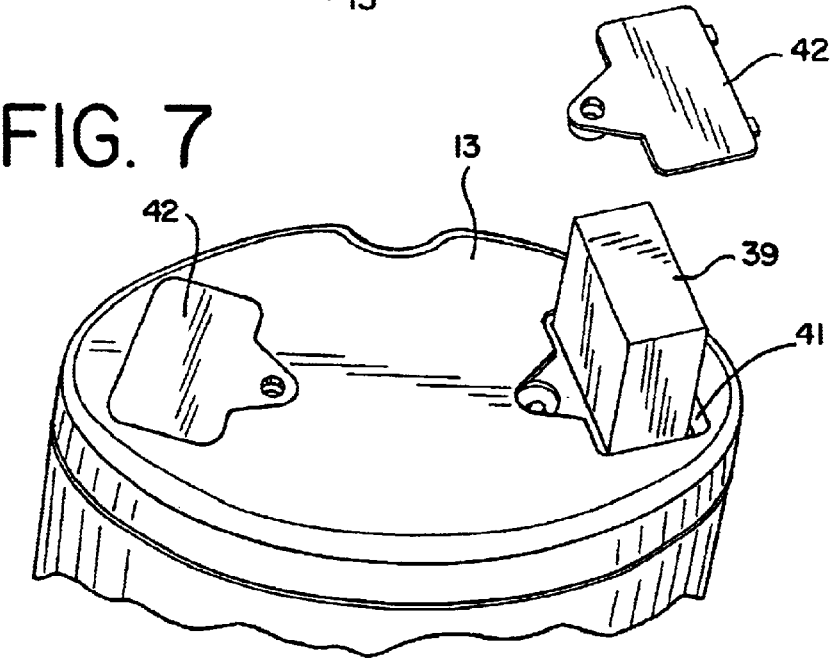
FIG. 7 is a bottom perspective view of the breastpump of FIG. 1 showing battery arrangement.

Power is provided either through ordinary house current via power cord 38, or electrochemical battery 39, such as a pair of 6V, 1.2 Ah lead-acid type rechargeable batteries. Power cord 38 is provided on a wrap-around mount conveniently located for storage in a well in the bottom of the lower housing part 13. FIG. 7 shows wells 41 formed within the lower housing 13 through which the batteries 40 are inserted into receptacles formed within the casing 10, having covers 42 for the wells. FIG. 7 omits the detail of the wrap mount 40, for clarity.

The Single Switch Inversely Controlling Vacuum and Rate

An on-off switch or knob 45 (and see FIG. 9) is provided on the casing, which can be rotary or push-button to that end. It is nonetheless rotary and push-button in this embodiment since it also acts to control the amount of vacuum being applied. The knob 45 (see FIG. 1) functions as a vacuum force adjustment device and as the knob 45 is rotated, a signal or vacuum control input is generated which increases or decreases the level of vacuum (suction force) to be applied, depending on which way the knob is turned. In this embodiment, as the suction force is increased, the cycle rate is decreased. That is, the rate and force are inversely related. This is considered to have a beneficial effect. The-knob is pushed in for on and off.

The Function Indicator

Additionally visible from the exterior of the casing 10 is a LCD display 48, a milk let-down button 49, and a program card slot 50 (the let-down sequence and programmable aspects will also be discussed in more detail below). Milk-let down button 49 is used to activate a pre-programmed suction sequence (embodied in components to be hereinafter described) particularly adapted for let-down and stimulate the milk ejection reflex. The slot 50 provides the interface access for programming cards used with the breastpump of this invention.

The display 48 provides visual indications of various functions of the pump. This could include, for example, the type of sequence then programmed, the level of suction force, the battery condition, and so forth.

The Diaphragm Protective Covers

In this embodiment, the two diaphragm pumps 30 are in a well formed in the top of the casing 10. A cover 35 (also 35' and 35" (again, primed numbers being substantially similar to their un-primed counterparts)) is provided which fits over the well and is generally flush with the upper housing part 11. The outlets 31 extend through relieved areas in the cover 35, for example, for easy access in use.

It may be noted that the shells 24 are shown formed in the cover of the embodiment of FIG. 8. The FIG. 17 embodiment has the shells 24 mounted in a removable manner in the upper housing, as through a snap fit or interference engagement, such as shown in the embodiment of FIGS. 20 and 21(*a*) through 21(*c*), to allow easier access for cleaning or replacing the membranes of the pumping mechanism, and for cleaning the shells themselves (which are provided with grips 33 to these ends).

In the FIG. 17 embodiment, diaphragm member or membrane 34, which may be made of any suitably durable flexible and durable fluid-impervious material (to be airtight), such as silicone with a Shore A hardness in the range of 30 to 70, is molded around its perimeter to a rigid plastic collar 85. Collar 85 has a plurality of depending anchor posts 86 with outboard flanges formed thereon, which engage with the inside lip of the respective well in the upper housing part 11 within which the collar 85 is received to snap-fit the membrane 34 in place.

Prophylactic (protective) disposable/cleanable covers 36 are additionally and advantageously provided, which form-fit over the diaphragms 34 and isolate them from air and other fluid from the breastshields. The covers 36, which can be made of the same material as the membranes but thinner, are likewise fluid-impervious.

Figure 20:
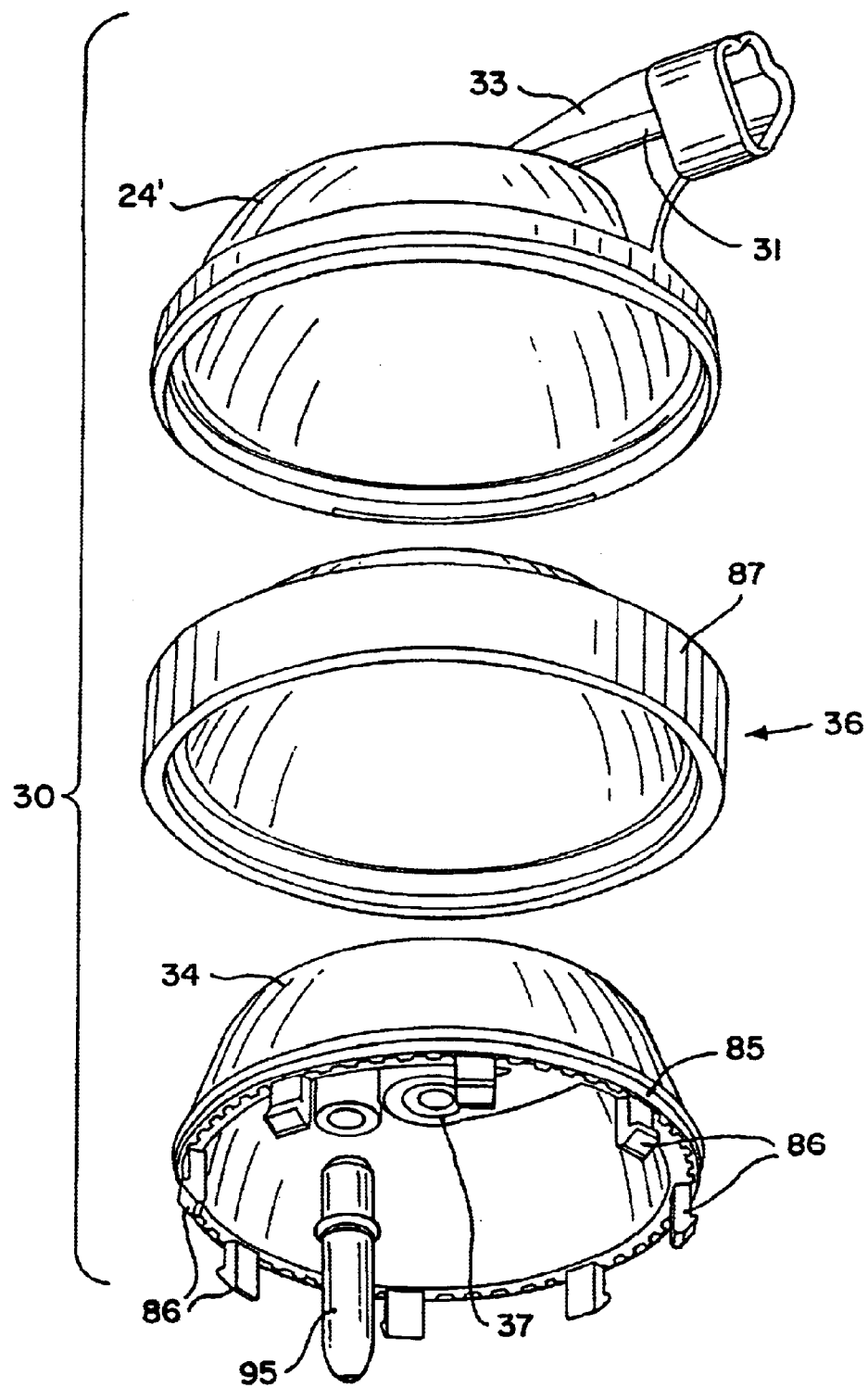
FIG. 20 is an enlarged assembly view of the diaphragm pump mechanism.
Figure 21A:
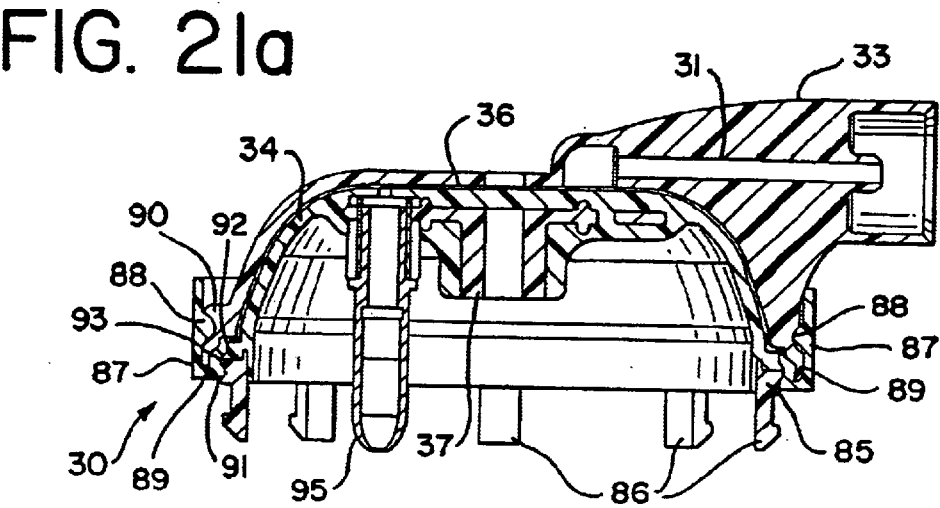
FIG. 21(*a*) is a cross-sectional view of the assembled diaphragm pump of FIG. 20.
FIG. 21(b) is an elevational view of the assembled diaphragm pump of FIG. 20.
FIG. 21(c) is a top view of the assembled diaphragm pump of FIG. 20.
Figure 21B:
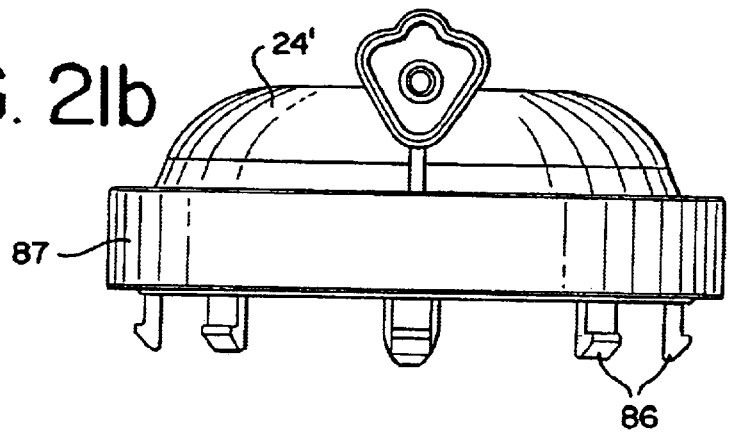
Figure 21C:
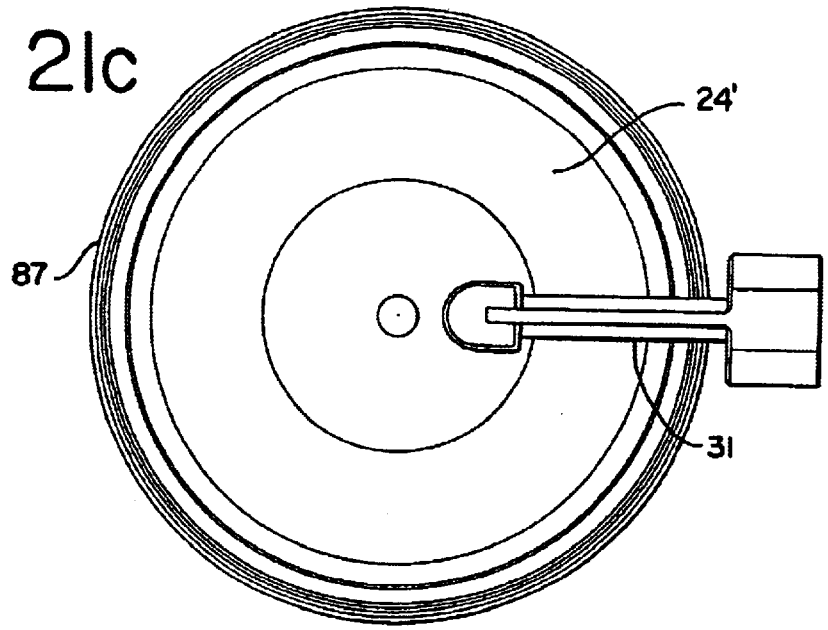

Referring to FIGS. 20 and 21(*a*) through 21(*c*) in particular, each of the covers 36 has an upturned cuff 87 which forms an annular well around the perimeter of the cover 36. A pair of circumferential beads 88 and 89, which are slightly offset vertically from each other, are formed along the bottom area of the annular well. Uppermost bead 88 engages in an annular rim channel 90 formed along the bottom outside of shell 24', for a substantially airtight engagement between the protective cover 36 and the shell.

An interior channel 93 is formed within the interior bottom of the cover 36 by a bead 91 and shoulder 92, which each run circumferentially around the cover. This interior channel 93 is received on a slightly protruding edge or rim on the collar 85 of the membrane 34. An airtight fit is thus provided between the protective cover 36 and the membrane 34, which also serves to releasably fix the shell 24 in place over the membrane 34, and complete the diaphragm pump 30.

Note also that a one-way valve 95 is provided in the membrane 34, which communicates with the possible space that may form between the membrane 34 and overlying cover 36. This valve permits any entrapped air therebetween to be exhausted, such as if the first stroke on start-up happens to be toward the shell 24, with the protective cover 36 thereafter then following the movement of the diaphragm 34 to which it will generally be in facial engagement.

The Programmable Aspects

Figure 9:
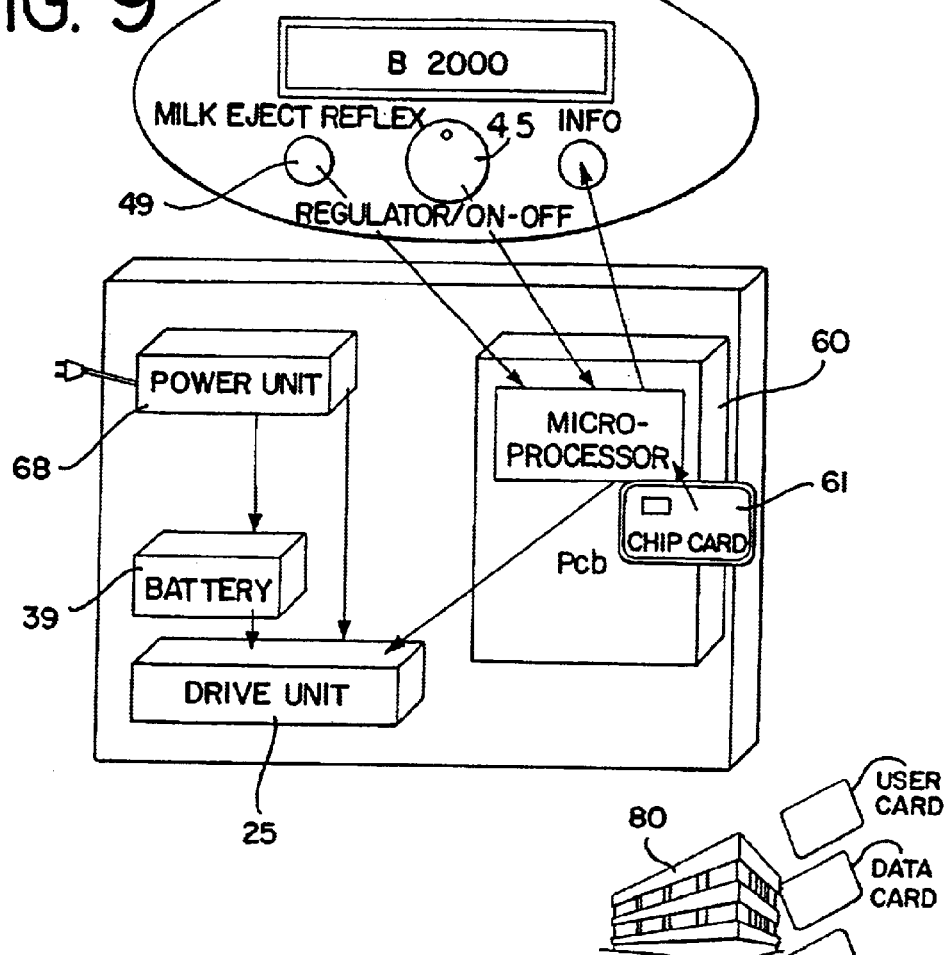
FIG. 9 is a diagrammatic representation of the interaction of various components with the controller.

One significant aspect of the present invention is the ability to program the breastpump with different types of suction sequences, or cycles as they are sometimes referred to herein. With reference to FIG. 9, for instance, the breastpump utilizes a microprocessor-based system indicated at 60 which is provided user input through a plurality of "chip" cards 61. Each chip card contains one or more predetermined programs recorded on an EEPROM. For example, each card could contain a specific type of sequence along with a milk let-down sequence.

An EEPROM microcontroller of the type MB90562 may be used, for one example, or the Atmel 2-wire EEPROM chipcard microcontroller AT24C164 for another. These provide about 16K of memory, which is considered presently sufficient.

The programs (some examples of which are described hereafter) are recorded in a conventional manner, and would be provided to the mother ready to use. The programmed chip card is inserted into the slot 50 in the back of the casing 10, where it engages an interface to the microprocessor. The particular program on the selected chip card 61 is then communicated to the microprocessor 60. Microprocessor 60 is integrated with the drive unit 25 to effect operation of the drive unit in accordance with the selected program, drawing upon either the AC power source as converted via standard technology to DC (indicated at 68 in FIG. 9), or from the battery source 39. The microprocessor 60 can also control power management.

Suction force (e.g., the amount of negative pressure generated) will typically also be adjustable by the user via operation of the rotary control knob 45, as noted above. A pre-set range for the suction force will nonetheless ordinarily be provided in the program as an initial setting, for adjustment by the user thereafter via the knob 45.

One embodiment contemplated provides a milk let-down sequence (milk ejection reflex) that can be engaged without need of a chip card for the same. The milk let-down sequence (described below) is pre-programmed in the microprocessor 60, or may otherwise be wired into the circuitry in a manner to override the then-existing operating program. When the mother desires to engage this sequence, she presses the button 49, which produces and sends an electrical signal, as to the microprocessor 60. The let-down program is then effected.

It will be readily understood that a chip card 61 is but one way to program the microprocessor 60. Other input means could be used, such as more dedicated buttons like button 49, each set to actuate a given sequence pre-programmed into the microprocessor 60. A numeric pad could be provided to input a code. The programs could be provided through an electronic data link, such as a modem, or optically, or otherwise.

Data can also be recorded by the microprocessor for downloading or transfer to the chip card. Data could also be directly recorded on the chip card. For instance, it is contemplated that the suckling action of a particular child could be recorded and reduced to a sequence. That sequence could then be programmed into the pump, and the mother would then have a suckling action from the pump very reminiscent of her own child.

Figure 10:
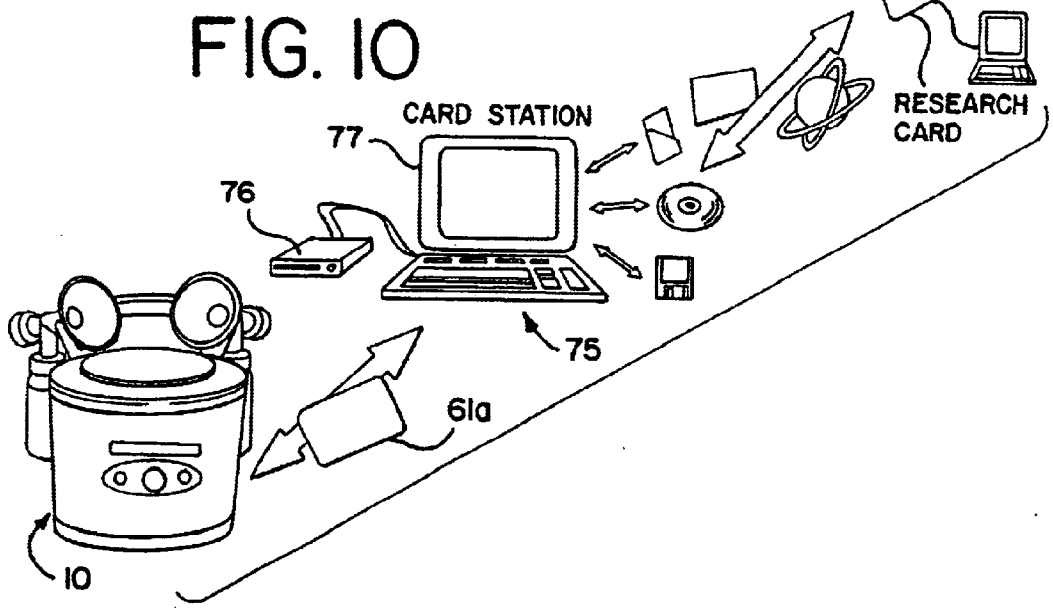
FIG. 10 is a schematic-type representation of a data storage and retrieval process that can be effected in accordance with the present invention.

Referring now to FIG. 10, the chip card 61a with breastpump operation data thereon is then read (downloaded) at a "card station" 65, shown here as a card reader 76 linked to a computer 77. The computer 77 is used to transfer the data to one of a variety of available media, such as CD, floppy disk, etc. for physical transfer to a research or data monitoring facility, here indicated at 80. The data could also simply be transferred via modem through an Internet interface.

The New Expression Methods (Cycles)

It can thus be seen that a variety of different suction cycles or sequences can now be provided with the same breastpump equipment. An example of the kind of methods that such cycle could represent comprises FIGS. 11 through 15.

Figure 11:
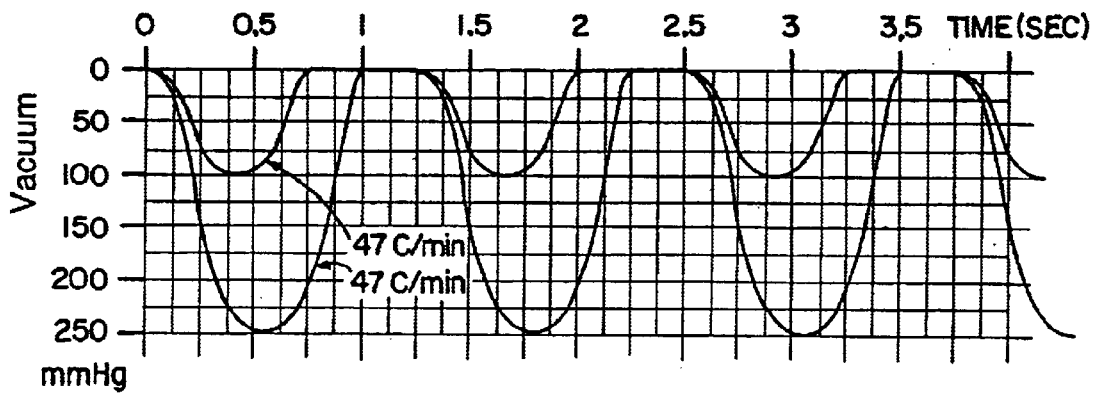

FIG. 11, for instance, is what is referred to by Medela, Inc. as the "Standard Classic Program". This is a method for operating a breastpump that has been developed which is considered to provide a general optimal suction curve reminiscent of an infant's normal suckling, such as provided by the 015 "CLASSIC" breastpump sold by Medela, Inc. As indicated in the graph of FIG. 11, negative pressure is along the y-axis (in millimeters of mercury) and time (in seconds) along the x-axis. In this particular method, the cycles are fixed at about 47 per minute; the amount of suction is generally adjustable between about 100 to about 250 mmHg.

Figure 12:
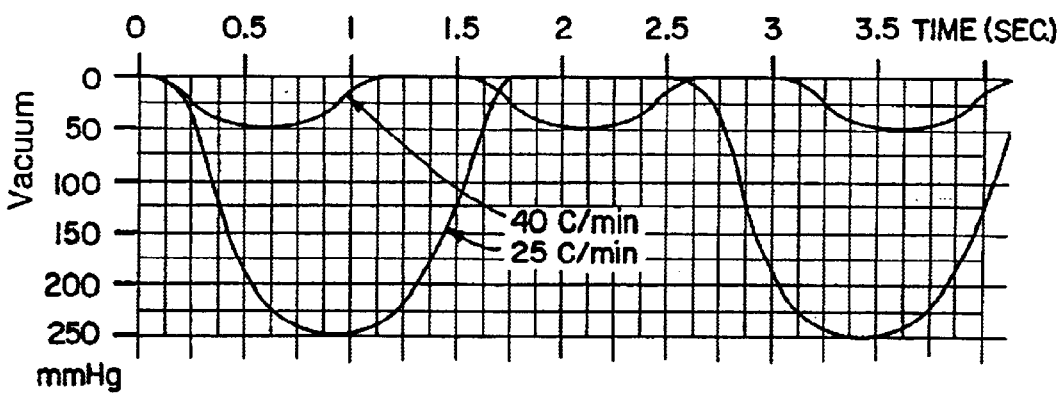

FIG. 12 illustrates what can be termed as a new "Sore Nipple Program" method. In comparison to FIG. 11, it will be seen that the lower end of the vacuum range is reduced to about 20 mmHg, and the overall suction cycle is extended in duration, i.e., from a low of about 25 cycles/min. to about 40. For a lower vacuum applied in this program, there is an increase in the number of cycles. In general, however, there is a slower and gentler suction compared with the "CLASSIC" program of FIG. 11.

FIG. 13 shows a new method for operating a breastpump which is considered to yield an increase in milk output. This is a program that might be applied between regular pump sessions several times a day. In this method, the breastpump is operated at a rapid cyclical tate on the order of about 120 cycles/min., preferably with a pause after a period of vacuum application; here, 10 seconds of vacuum, then a 2 second pause. The negative pressure is in the range of about 50 to about 150 mmHg. Note the detail in the inset of FIG. 13 showing the rapidity and steep slopes of the vacuum application.

What has been termed a new "Superior Program" for operating a breastpump is illustrated in FIG. 14. A vacuum range of about 100 to about 250 mmHg has been chosen, with cycles ranging from about 47 to about 78 per minute. The cycle rate and the vacuum are tied, such that as, for instance, the cycles decrease, the amount of vacuum increases, i.e., there is an inverse relationship. It will be noted that this program differs from the "CLASSIC" program above in part through a sequence that initially reaches a peak negative pressure, then smoothly starts a pressure increase (less negative) along a similar (although opposite) slope to that of the negative pressure build-up, but then slows the pressure increase briefly, before continuing on essentially the initial slope for the negative pressure release. A milk let-down sequence is also incorporated in this "Superior Program," and utilizes a vacuum range of about 50 to about 150 mmHg, with cycles ranging between about 80 to about 160 per minute.

Thus, while the invention has been described herein with relation to certain embodiments and applications, those with skill in this art will recognize changes, modifications, alterations and the like which still come within the spirit of the inventive concept, and such are intended to be included within the scope of the invention as expressed in the following claims.

What is claimed is:

1. A vacuum pump for a breastpump comprising:
   a source of vacuum for applying a level of vacuum force;
   a motor drive for said source of vacuum;
   a mechanism which alters the level of vacuum force from said source of vacuum, and which varies a rate of vacuum application;
   a controller, said controller providing a rate control input to said mechanism and a level control input to said mechanism such that said vacuum force is varied according to an inverse relationship with said rate, and
   a single manually operated switch operatively connected to said controller, said switch providing an input to said controller over a range that simultaneously adjusts said vacuum force and said rate according to said inverse relationship.

2. The pump of claim 1 wherein said switch is a manually manipulated rotary knob.

3. The pump of claim 2 wherein rotation of said knob produces a signal which varies with the position of said knob, said knob when rotated in one direction producing a signal for increasing said rate while also decreasing said vacuum.

* * * * *